United States Patent
Rosenberg (10) Patent No.: US 10,345,338 B2
(45) Date of Patent: Jul. 9, 2019

(54) TEST CAP FOR A CABLE

(71) Applicant: Biosense Webster (Israel) Ltd., Yokneam (IL)

(72) Inventor: Avigdor Rosenberg, Kiryat Tivon (IL)

(73) Assignee: Biosense Webster (Israel ) Ltd., Yokneam (IL)

( * ) Notice: Subject to any disclaimer, the term of this patent is extended or adjusted under 35 U.S.C. 154(b) by 634 days.

(21) Appl. No.: 14/860,060

(22) Filed: Sep. 21, 2015

(65) Prior Publication Data

US 2017/0082655 A1 Mar. 23, 2017

(51) Int. Cl.
*G01R 1/04* (2006.01)
*G01R 31/02* (2006.01)
*H01R 13/66* (2006.01)
*G01R 31/28* (2006.01)

(52) U.S. Cl.
CPC ......... *G01R 1/0416* (2013.01); *G01R 31/021* (2013.01); *G01R 31/2844* (2013.01); *H01R 13/665* (2013.01); *A61B 2560/0266* (2013.01); *A61B 2562/16* (2013.01); *G01R 31/024* (2013.01)

(58) Field of Classification Search
CPC ............................ G01R 1/0416; G01R 31/024; G01R 31/2844; G01R 31/021; A61B 2562/16; A61B 2560/0266; H01R 13/665
USPC ..... 324/754.03, 500, 754.05, 425, 437, 445, 324/446, 754.07, 754.1–754.21, 755.01, 324/756.03, 758.01, 690, 696, 715
See application file for complete search history.

(56) References Cited

U.S. PATENT DOCUMENTS

| | | | |
|---|---|---|---|
| 3,906,477 A | 9/1975 | Schweitzer, Jr. | |
| 5,566,680 A * | 10/1996 | Urion | A61B 5/035 600/561 |
| 7,816,925 B1 | 10/2010 | Gale | |
| 2006/0073728 A1 | 4/2006 | Zaiken et al. | |
| 2011/0136396 A1 | 6/2011 | Burwell et al. | |
| 2013/0226254 A1 | 8/2013 | Walling et al. | |

FOREIGN PATENT DOCUMENTS

| | | |
|---|---|---|
| GB | 2 448 879 A | 11/2008 |
| WO | WO 92/14216 A1 | 8/1992 |

OTHER PUBLICATIONS

European Search Report dated Feb. 3, 2017, Application No. EP 16 18 9724.

* cited by examiner

*Primary Examiner* — Melissa J Koval
*Assistant Examiner* — Trung Nguyen (57) ABSTRACT

An electronic device includes a housing, which is sized and shaped to fit snugly over a connector containing first electrical contacts at an end of a cable. The electronic device further includes second electrical contacts within the housing and test circuitry. The second electrical contacts are configured and positioned to mate with the first electrical contacts when the housing is fitted over the connector. The test circuitry is contained within the housing and coupled to the second electrical contacts and configured to test a functionality of the cable.

26 Claims, 5 Drawing Sheets

TEST CAP FOR A CABLE

FIELD OF THE INVENTION

The present invention relates generally to testing electrical cables, and specifically to test caps and adapters for cables.

BACKGROUND OF THE INVENTION

Electrical cables are used in a wide range of electronic applications. Cables are sometimes subjected to functionality tests. Examples prior art techniques for testing electrical cables are provided below.

U.S. Patent application publication 2011/0136396, whose disclosure is incorporated herein by reference, describes a re-enterable end cap for sealing and protecting an end of an exposed cable conductor while allowing repeated access to the cable by a metal test probe. The end cap has an outer tubular shell which is open at one end to receive the end of the cable and closed at the opposite end by a plug of rigid material. The tubular shell may be dimensionally recoverable. The plug has a hollow cavity which contains a deformable self-sealing material.

U.S. Pat. No. 3,906,477, whose disclosure is incorporated herein by reference, describes a plug-in connector for high voltage alternating current circuits includes a conductor embedded in insulating material with a test point terminal capacitively associated therewith together with fault responsive means mounted on the connector and having a target that is shifted to fault indicating position on flow of fault current in the conductor and is reset from the fault indicating position on restoration of energizing voltage to the conductor.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention that is described herein provides an electronic device including a housing, which is sized and shaped to fit snugly over a connector containing first electrical contacts at an end of a cable. The electronic device further includes second electrical contacts within the housing, and test circuitry. The second electrical contacts are configured and positioned to mate with the first electrical contacts when the housing is fitted over the connector. The test circuitry is contained within the housing and coupled to the second electrical contacts, and configured to test a functionality of the cable.

In some embodiments, the electronic device includes a mechanical interface for attaching the housing to the connector. In other embodiments, the electronic device is built as part of the connector. In yet other embodiments, the test circuitry is configured to receive electrical power from an internal battery.

In an embodiment, the electronic device is configured to connect, via the cable, to an electronic system at an opposite end of the cable when the housing is fitted over the connector. In another embodiment, the test circuitry is configured to receive electrical power from the electronic system via the cable. In yet another embodiment, the electronic device is configured to test a functionality of the electronic system.

In some embodiments, the test circuitry is configured to display test results on a display of the electronic system. In other embodiments, the electronic device further includes a display, which is configured to display test results locally at the electronic device. In yet other embodiments, the display includes one or more visual indicators. In an embodiment, the housing is configured to cover the connector so as to protect the connector from mechanical damage. In another embodiment, the electronic device is configured to be sterilized or autoclaved so as to be used in a medical environment.

In some embodiments, the electronic device additionally includes third electrical contacts, one or more switches and control circuitry. The third electrical contacts are configured for connecting to an additional cable. The one or more switches are configured to connect the second electrical contacts to the testing circuitry in a testing mode, and to connect the second electrical contacts to the third electrical contacts in a pass-through mode. The control circuitry is configured to control the switches. In other embodiments, the control circuitry is configured to be instructed to select between the testing mode and the pass-through mode over the cable.

There is additionally provided, in accordance with an embodiment of the present invention, a method for cable testing including fitting an electronic device over a connector at an end of a cable, the connector containing first electrical contacts, such that a housing of the electronic device fits snugly over the connector and second electrical contacts of the electronic device, within the housing, are positioned to mate with the first electrical contacts. A functionality of the cable is tested using test circuitry of the electronic device, which is contained within the housing and coupled to the second electrical contacts.

The present disclosure will be more fully understood from the following detailed description of the embodiments thereof, taken together with the drawings, in which:

DETAILED DESCRIPTION OF EMBODIMENTS

Overview

Embodiments of the present invention that are described herein provide an electronic device and a method for testing an electrical cable, e.g., during the setup or regular operation of an electronic system. Functionality testing for a cable may involve continuity testing of the cable parts (e.g., wires and connector pins), impedance and resistance of the wires comprised in the cable, inter-wire characteristics, or other suitable tests.

In some disclosed embodiments, a testing device is attached to a connector at the end of a cable using a mechanical interface. The testing device comprises a housing that is attached to the mechanical interface and comprises electrical contacts, such as connecting pins, which are configured to mate with electrical contacts comprised in the connector, so as to conduct electrical signals between the connector and the device. The device further comprises test circuitry, which is configured to test the functionality of the cable. For example, the test circuitry may send and receive electrical signals to and from the electrical contacts, analyze the signals and to provide functionality status of the cable.

In an embodiment, the test circuitry may comprise a display that displays results of the functionality test of the cable. The display may comprise one or more visual indicators to indicate the functionality status of the cable when the test completes and possibly during the test.

In another embodiment, during testing, the testing device connects to one end of the cable, and the cable is connected at the other end to an electronic module, such as an operating console. The console sends testing signals to the testing device via the cable and the electrical contacts comprised in the connector and in the testing device. In yet another embodiment, the test circuitry may not comprise a display and the functionality test results may be displayed on a screen of the operating console. In some embodiments, the operating console also provides electrical power for operating the testing device. In yet another embodiment, the testing device is made of durable materials and configured to withstand sterilization or autoclaving processes so as to be qualified for utilization in a medical environment.

The terms "module" and "sub-system" in the present disclosure are used interchangeably and refer to parts comprised in the electronic system, which are interconnected by the electrical cables.

In some embodiments, the testing device is used during the setup of the electronic system, for testing the functionality of the cable, while the cable is connected to the operating console at one end, and remains unconnected at the other end (e.g., distal end) of the cable that uses for connecting the console to a sub-system, such as a medical catheter.

In case of a failure, occurring while operating the electronic system, the distal end of the cable may be disconnected from the sub-system and connected to the housing of the testing device so as to test the functionality of the cable. During testing, the distal end of the cable is typically disconnected from the catheter so as to avoid interference with the medical procedure.

Typically, electronic modules such as operating consoles, comprise internal testing capabilities. In an embodiment, the testing device may be used for testing the functionality of front end circuits and sockets of the console, in addition to testing the functionality of the cable itself, by closing loop on the signals that are transmitted from the console, analyzing the signals to detect potential faults in the console, and sending the analyzed signals back to the console.

In some embodiments, the disclosed device is mechanically connected to a connector of the cable using a mechanical interface. After testing a first cable, the device may be detached from the connector of the first cable and shifted to a second connector of second cable so as to test the second cable. This technique saves costs since a single device may be used for testing multiple cables. In alternative embodiments, the connector may comprise a built-in device so as to save the time required to shift the device from one tested cable to another. In yet another embodiment, the device is implemented as an adapter that is connected in-line between two sections of cable, or between the cable and an electronic module.

The disclosed techniques may be used in any electronic system to shorten the time required to isolate and fix faults while saving costs caused by falsely replacing functional cables, or falsely replacing functional end devices, such as catheters, connected to the cable distal end.

System Description

Figure 1:
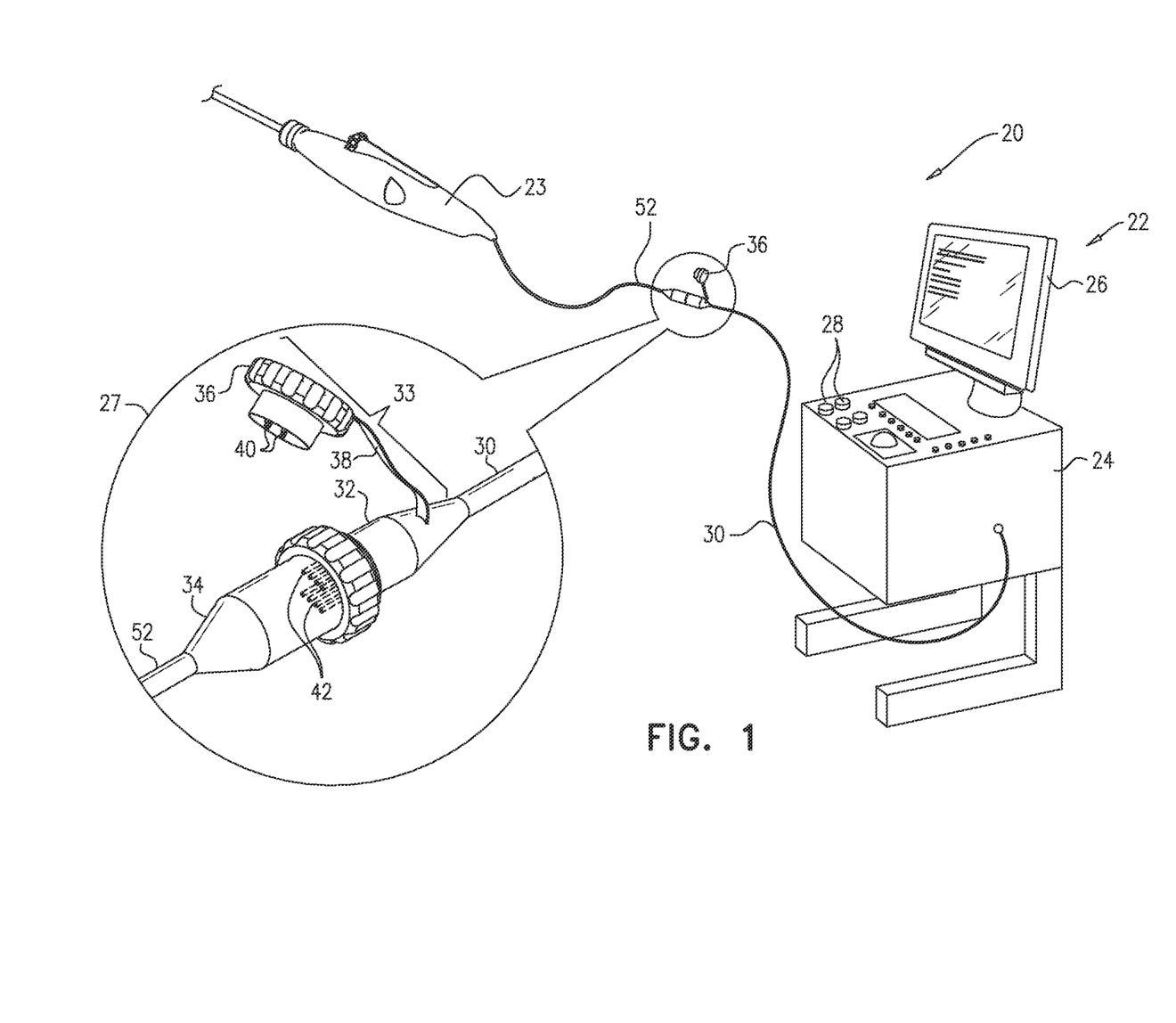
FIG. 1 is a schematic pictorial illustration of an electronic system, in accordance with an embodiment of the present invention.

FIG. 1 is a schematic pictorial illustration of an electronic system 20, in accordance with an embodiment of the present invention. System 20 comprises an operating console 22 and an electronic module 23, which are interconnected by electronic cables 30 and 52, respectively.

Console 22 comprises input devices 28, a display 26, and electronic circuitry 24 that comprises several circuits (not shown), such as an interface to module 23, a processor, front end circuits and sockets of the system console. Referring to an inset 27, a connector 32 is attached to a distal end of cable 30 and configured to connect to a mating connector 34 using electrical contacts 42.

A testing device 33 comprises a mechanical interface 38, in the present example a strap, which attaches to a housing 33 that is sized and shaped to fit snugly over connector 32. Device 33 further comprises electrical contacts 40, which are configured to connect to the electrical contacts of connector 32. Additional embodiments of housing 33 and contacts 40 are described in greater details in FIGS. 2-4.

Cable 52 is attached to connector 34 at its distal end, and plugged into module 23 at its proximal end. Alternatively, connector 34 may be an integral part of module 23, without cable 52. Module 23 may be any electronic module, such as a catheter used in medical procedures, a suitable communication device, or other suitable module.

In some embodiments, device 33 is made of durable materials (e.g., plastic) and configured to be sterilized or autoclaved so as to be used in a medical environment.

Figure 2:
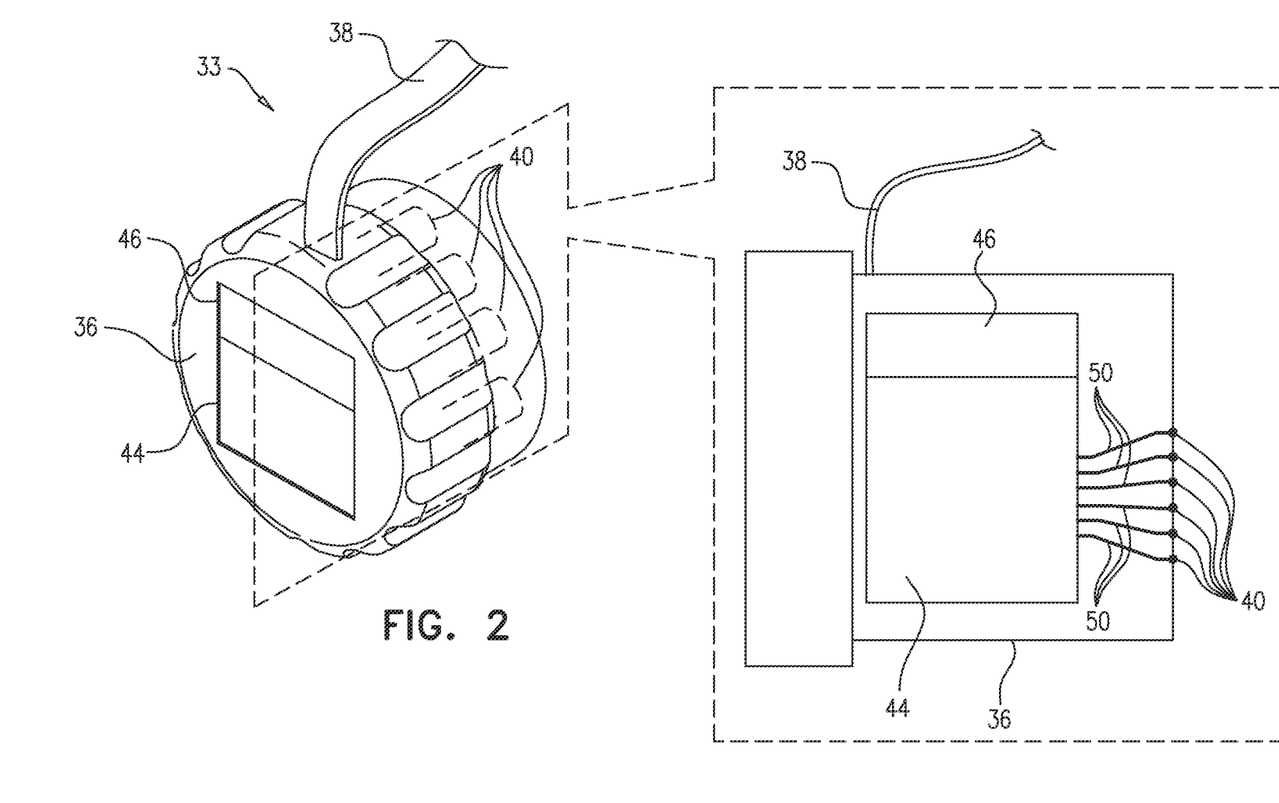
FIG. 2 is a schematic pictorial illustration of a testing device, in accordance with an embodiment of the present invention.

FIG. 2 is a schematic pictorial illustration of device 33, in accordance with an embodiment of the present invention. Housing 36 comprises electrical contacts 40, which are configured and positioned to mate with contacts 42 when the housing is fitted over connector 32. Typically, console 22 is configured to test the functionality of cable 30, and testing device 33 enables the testing by the console while the distal end of cable 30 is disconnected from cable 52 or from module 23 and connects instead to testing device 33.

In some embodiments, housing 36 comprises test circuitry 44, which is coupled to contacts 40 via wires 50, and configured to test the functionality of cable 30, including both the cable wires and contacts 42. The functionality test may comprise testing various properties of the wires such as the continuity of part or all of the cable wires and connector pins, impedance, resistance, and other characteristics of the wires comprised in cable 30, as well as inter-wire characteristics.

In various embodiments, test circuitry 44 may comprise any suitable type of electronic circuitry. In the present context, an electrical conductor such a short or loopback connection that shorts together two or more of contacts 40 is also regarded as test circuitry. Additionally or alternatively, test circuitry 44 may comprise, for example, passive net of resistors, or active integrated circuits generating test signals, or even a micro-controller, either operated by an internal battery or having its supply from console 24 through cable 30.

In an embodiment, the results of the functionality tests may be analyzed by console 22 and presented to a user on display 26 of console 22. In another embodiment, test circuitry 44 may comprise a display 46, which is configured to display the test results in a complete format as described for display 26, or in any other suitable format. In yet other embodiments, display 46 may comprise visual indicators, such as Light Emitting Diodes (LEDs), which are configured to display a functionality status of the cable using selected display arrangements of the indicators (for example, a red LED can indicate a fault state and a green LED can indicate that the test has passed).

In some embodiments, console 22 may recognize a connection of testing device 33 to cable 30 and may automatically initiate the testing of cable 30. Alternatively, device 33 may comprise a suitable input device (e.g., DIP switch or pushbutton(s)) for configuring or starting the test by a user.

Functionality test for cables may be performed before and/or during system operation. For example, during a medical procedure, it may become apparent to the user that there is a fault condition in one or more of the electronic modules comprised in the medical system used in the procedure. In some types of faults it is unclear which section of the medical system malfunctions, and a typical debug scenario is to sequentially replace different parts of the system until the fault is rectified. Typically, electronic modules of the system are interconnected using electrical cables. Since cables typically cost less than the electronic modules and are easy to replace, a user may attempt fixing the fault condition by falsely replacing one or more cables that are fully functional, thus, wasting time and money without solving the fault.

In some embodiments, device 33 may be attached, using mechanical interface 38 (or any other suitable interface), to connectors of selected cables comprised in the system, so as to provide the user with a built-in testing capability while setting up the medical procedure or while identifying a fault during performing the medical procedure. The described techniques may be applicable in additional applications, such as for testing cables while setting up a communication system, or during a communication session between multiple communication sub-systems.

Figure 3:
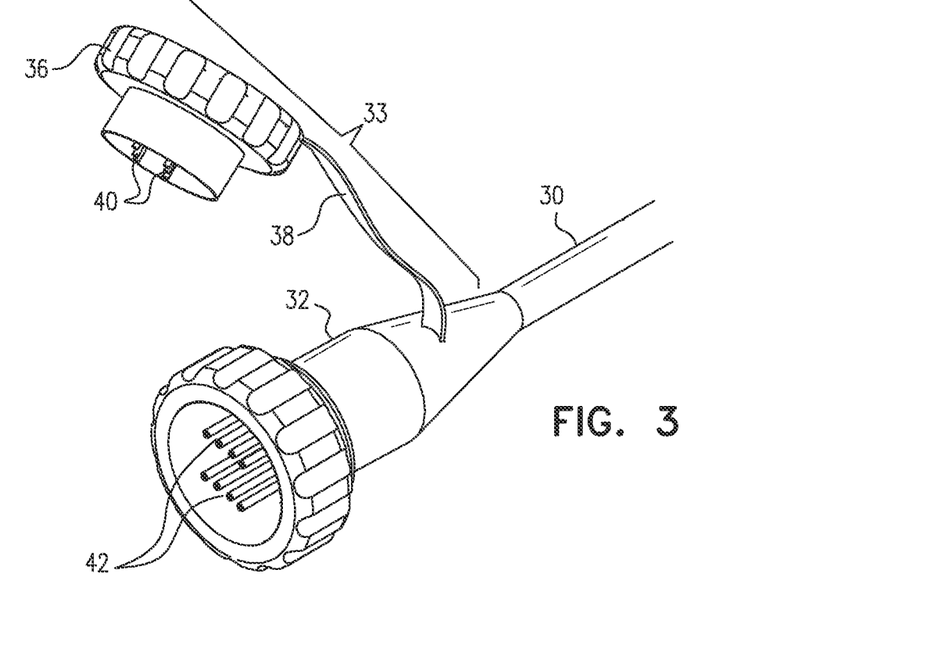
FIGS. 3 and 4 are schematic pictorial illustrations of a connector and a testing device that uses for testing the cable, in accordance with embodiments of the present invention.

FIG. 3 is a schematic pictorial illustration of device 33 in a detached position, in accordance with an embodiment of the present invention. In order to test cable 30, the user may disconnect cable 30 from cable 52 by separating between connectors 32 and 34 (shown in FIG. 1).

Figure 4:
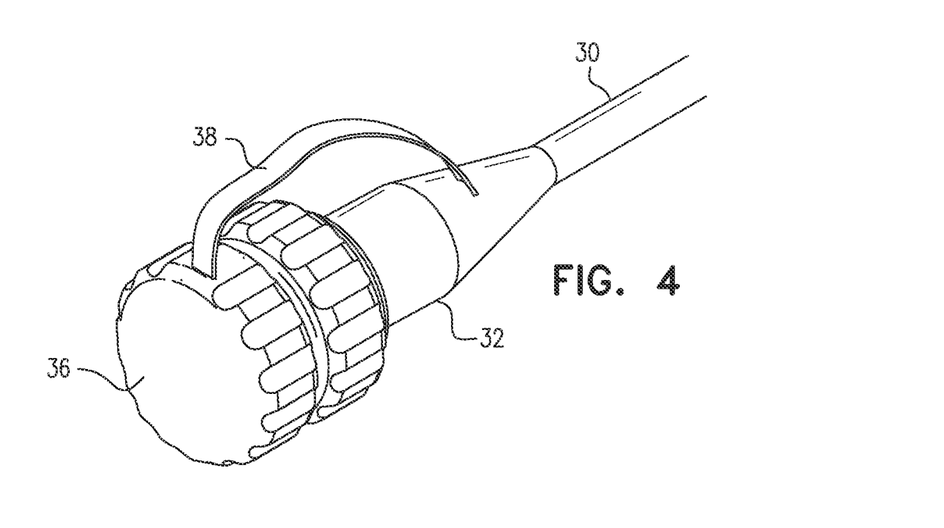

FIG. 4 is a schematic pictorial illustration of device 33 connected to connector 32, in accordance with an embodiment of the present invention. In this position, housing 36 fits over connector 32 so that contacts 40 are positioned to mate with contacts 42. The user may test the functionality of cable 30 using input devices 28 and electronic circuitry 24, which is configured to send testing signals to test circuitry 44 via cable 30 and electrical contacts 42 and 40. In an embodiment, test circuitry 44 is configured to analyze the testing signals and to generate the functionality test status of the cable, which may be displayed on displays 46 and/or 26. In an embodiment, test circuitry 44 may be used for testing the functionality of front end circuits and sockets comprised in the console.

Figure 5:
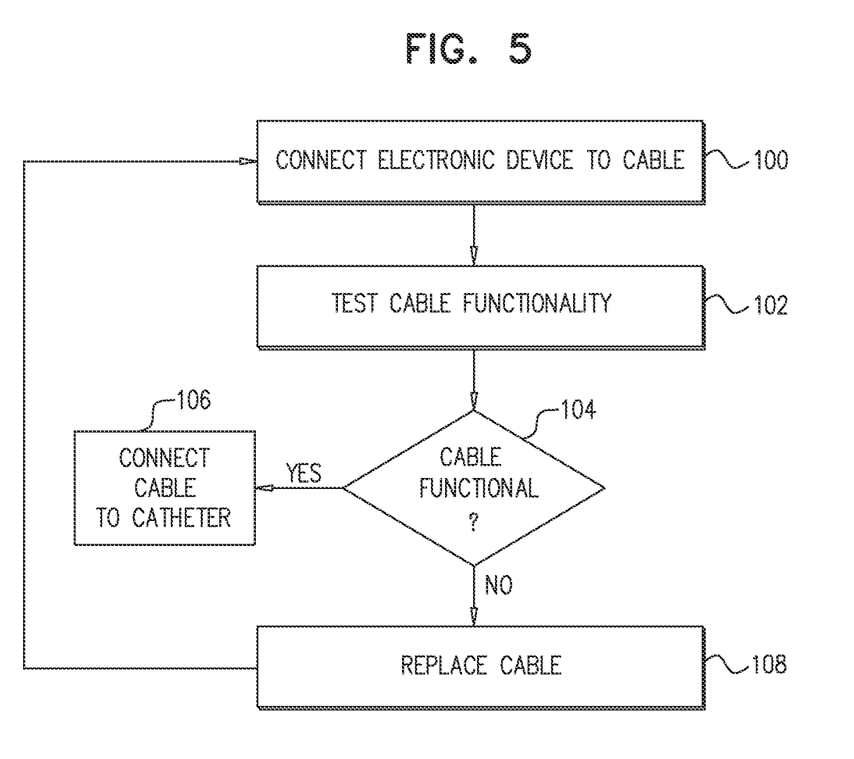
FIG. 5 is a flow chart that schematically illustrates a method for testing a cable using a testing device, in accordance with an embodiment of the present invention.

FIG. 5 is a flow chart that schematically illustrates a method for testing cable 30 using device 33, in accordance with an embodiment of the present invention. The method begins with connecting testing device 33 to cable 30 via connector 32, at a device connecting step 100. In an embodiment, connecting testing device 33 to cable 30 can be carried out during setting up the system so as to verify that cable 30 is functional prior to operating system 20. For example, the test is performed after connecting cable 30 to circuitry 24 and prior to connecting cable 30 to module 23. In an alternative embodiment, in response to a failure in system 20, cable 30 can be disconnected from cable 52 (or directly from module 23) and connected to device 33 so as to identify whether cable 30 is the source of the failure.

In some embodiments, circuitry 24 checks the electrical connectivity between electrical contacts 40 and 42, and the user initiates the functionality test of the cable using input devices 28. Electrical circuitry 44 receives the testing signals from circuitry 24, via cable and contacts 40 and 42, analyzes the signals, and displays 22 and/or 46 display the results of the functionality test, at a testing step 102. At a decision step 104, in some embodiments, in response to the test results (e.g., continuity of all wires (not shown) in cable 30, continuity of contacts 42, impedance and resistance of the wires and between wires) the user may decide whether the cable is functional or not. In other embodiments, displays 22 and/or 46 may automatically display a functional/non-functional outcome of the test, for example by lighting a green LED to display functionality, or a red LED to display non-functionality.

If the cable passes the test successfully, housing 36 is pulled-out from connector 32 and connector 32 is connected to an electronic module 23 (e.g., an insertion catheter used in a medical procedure) via connector 34, at a connecting to catheter step 106. On the other hand, if the cable fails the test, the cable is considered non-functional and can be replaced with another, substantially similar cable, at a cable replacement step 108. In some embodiments, after replacing the cable the method may loop back to device connecting step 100 so as to test the functionality of the replacing cable.

Figure 6:
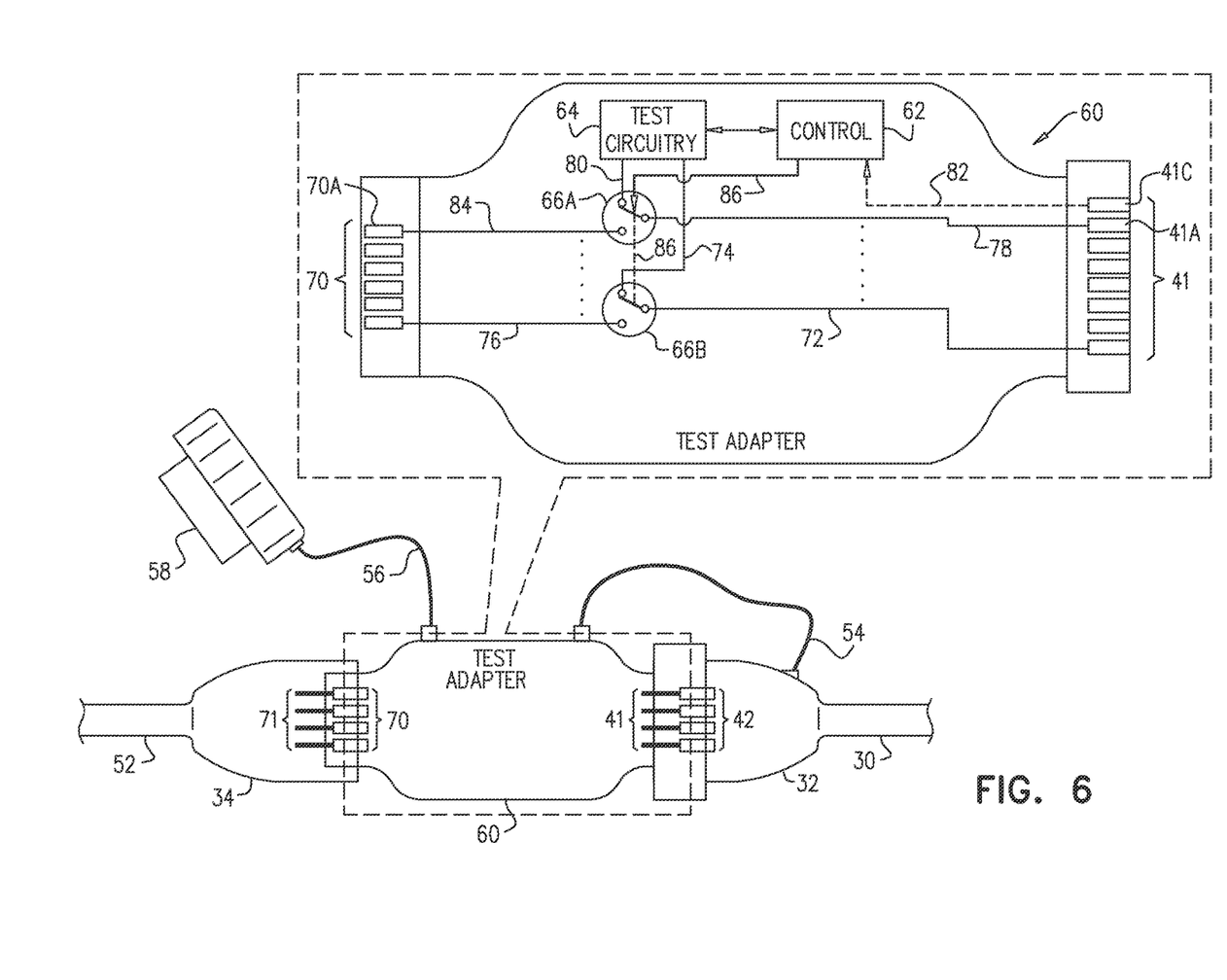
FIG. 6 is a schematic pictorial illustration of a testing device, in accordance with another embodiment of the present invention.

FIG. 6 is a schematic pictorial illustration of a testing device, in accordance with another embodiment of the present invention. The testing device in this example is implemented as a testing adapter 60, which is electrically connected to connectors 32 and 34 as described in FIG. 1. In an embodiment, adapter 60 may comprise an optional mechanical interface 54 that mechanically connects the adapter to connector 32. In another embodiment, adapter 60 may comprise a mechanical interface 56 that connects adapter 60 to an optional protecting cover 58, which is configured to fit snugly over adapter 60 (when connector 34 is disconnected from adapter 60) so as to mechanically protect the adapter. The test adapter comprises electrical contacts 41, which are configured and positioned to mate with contacts 42 when the adapter is fitted over connector 32. Adapter 60 further comprises electrical contacts 70 that are similarly configured and positioned to mate with electrical contacts 71 of connector 34.

Referring to an inset 61, adapter 36 comprises test circuitry 64, which is substantially similar to test circuitry 44 as described in FIG. 2. Test circuitry 64 is configured to perform functional tests to the cable in question as described in FIGS. 1-5. A relay 66 comprises one or more switches, such as switches 66A and 66B that are controlled by a controller 62. Typically the controller changes the states of all the switches simultaneously. In alternative embodiments, each switch may be controlled separately.

Switch 66A is connected to a contact 41A via a wire 78, to a contact 70A via a wire 84, and to test circuitry via a wire

80. Switch 66A is configured to switch between connecting contact 41A to test circuitry 64 in a testing mode, or to contact 70A in a pass-through mode. Similarly, switch 66B is connected to another of contacts 41 via a wire 72, to another of contacts 70 via a wire 76, and to test circuitry 64 via a wire 74. Switch 66B is configured to switch its respective contact 41 to test circuitry 64 in the testing mode, or to its respective contact 70 in the pass-through mode.

In the testing mode, test circuitry 64 performs the testing of cable 30 as described above. In the pass-through mode, switches 66A and 66B disconnect test circuitry 64 and connects contacts 41 to contacts 70 so as to allow normal operation of system 20. Switches 66A and 66B are further connected, via a wire 86, to controller 62, which is configured to control the switches. In some embodiments, console 22 may send switching commands to controller 62 via cable 30, using a contact 41C and a wire 82. In alternative embodiments, the controller may be controlled using an internal timer (not shown).

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. An electronic device, comprising:
   a housing, which is sized and shaped to fit snugly over a connector at an end of a cable, the connector containing first electrical contacts;
   second electrical contacts within the housing, which are configured and positioned to mate with the first electrical contacts when the housing is fitted over the connector;
   test circuitry, which is contained within the housing and coupled to the second electrical contacts and configured to test a functionality of the cable;
   third electrical contacts for connecting to an additional cable;
   one or more switches, configured to connect the second electrical contacts to the testing circuitry in a testing mode, and to connect the second electrical contacts to the third electrical contacts in a pass-through mode; and
   control circuitry, configured to control the switches.

2. The electronic device according to claim 1, wherein the electronic device comprises a mechanical interface for attaching the housing to the connector.

3. The electronic device according to claim 1, wherein the electronic device is built as part of the connector.

4. The electronic device according to claim 1, wherein the test circuitry is configured to receive electrical power from an internal battery.

5. The electronic device according to claim 1, wherein the electronic device is configured to connect, via the cable, to an electronic system at an opposite end of the cable, when the housing is fitted over the connector.

6. The electronic device according to claim 5, wherein the test circuitry is configured to receive electrical power from the electronic system via the cable.

7. The electronic device according to claim 5, wherein the electronic device is configured to test a functionality of the electronic system.

8. The electronic device according to claim 5, wherein the test circuitry is configured to display test results on a display of the electronic system.

9. The electronic device according to claim 1, and comprising a display, which is configured to display test results locally at the electronic device.

10. The electronic device according to claim 9, wherein the display comprises one or more visual indicators.

11. The electronic device according to claim 1, wherein the housing is configured to cover the connector so as to protect the connector from mechanical damage.

12. The electronic device according to claim 1, wherein the electronic device is configured to be sterilized or autoclaved so as to be used in a medical environment.

13. The electronic device according to claim 1, wherein the control circuitry is configured to be instructed to select between the testing mode and the pass-through mode over the cable.

14. A method for cable testing, comprising:
   fitting an electronic device over a connector at an end of a cable, the connector containing first electrical contacts, such that a housing of the electronic device fits snugly over the connector and second electrical contacts of the electronic device, within the housing, are positioned to mate with the first electrical contacts; and
   testing a functionality of the cable using test circuitry of the electronic device, which is contained within the housing and coupled to the second electrical contacts;
   connecting the electronic device to an additional cable via third electrical contacts;
   using one or more switches, connecting the second electrical contacts to the testing circuitry in a testing mode; and
   connecting the second electrical contacts to the third electrical contacts in a pass-through mode.

15. The method according to claim 14, wherein the housing is attached to the connector using a mechanical interface.

16. The method according to claim 14, wherein the electronic device is built as part of the connector.

17. The method according to claim 14, and comprising receiving electrical power to the electronic device from an internal battery.

18. The method according to claim 14, and comprising connecting the electronic device, via the cable, to an electronic system at an opposite end of the cable.

19. The method according to claim 18, and comprising receiving electrical power from the electronic system via the cable.

20. The method according to claim 18, and comprising testing a functionality of the electronic system.

21. The method according to claim 18, wherein testing the functionality comprises displaying test results on a display of the electronic system.

22. The method according to claim 14, wherein testing the functionality comprises displaying test results on a display of the electronic device.

23. The method according to claim 22, wherein the display comprises one or more visual indicators.

24. The method according to claim 14, and comprising covering the connector, using the housing, so as to protect the connector from mechanical damage.

25. The method according to claim 14, and comprising sterilizing or autoclaving the electronic device so as to be used in a medical environment.

26. The method according to claim 14, and comprising receiving instructions to select between the testing mode and the pass-through mode over the cable.

* * * * *